US011433237B2

(12) United States Patent
Lovett (10) Patent No.: US 11,433,237 B2
(45) Date of Patent: Sep. 6, 2022

(54) NEUROMODULATION THERAPY FOR AUTO-IMMUNE AND INFLAMMATORY DISORDERS

(71) Applicant: LivaNova USA, Inc., Houston, TX (US)

(72) Inventor: Eric Lovett, Houston, TX (US)

(73) Assignee: LivaNova USA, Inc., Houston, TX (US)

( * ) Notice: Subject to any disclaimer, the term of this patent is extended or adjusted under 35 U.S.C. 154(b) by 313 days.

(21) Appl. No.: 16/711,309

(22) Filed: Dec. 11, 2019

(65) Prior Publication Data
US 2020/0188671 A1  Jun. 18, 2020

Related U.S. Application Data

(60) Provisional application No. 62/779,344, filed on Dec. 13, 2018.

(51) Int. Cl.
*A61N 1/36* (2006.01)
(52) U.S. Cl.
CPC ....... *A61N 1/36053* (2013.01); *A61N 1/3606* (2013.01); *A61N 1/3611* (2013.01); *A61N 1/36078* (2013.01); *A61N 1/36117* (2013.01); *A61N 1/36139* (2013.01)
(58) Field of Classification Search
CPC .............. A61N 1/36053; A61N 1/3606; A61N 1/36078; A61N 1/3611; A61N 1/36117; A61N 1/36139; A61B 5/0205; A61B 5/4812; A61B 5/4836; A61B 5/686
See application file for complete search history.

(56) References Cited

U.S. PATENT DOCUMENTS

| | | | |
|---|---|---|---|
| 5,335,657 A | 8/1994 | Terry, Jr. et al. | |
| 7,155,278 B2 | 12/2006 | King et al. | |
| 7,228,167 B2 | 6/2007 | Kara et al. | |
| 8,600,505 B2 | 12/2013 | Libbus et al. | |
| 10,265,523 B2 | 4/2019 | Simon et al. | |
| 2008/0058873 A1* | 3/2008 | Lee .......................... | A61B 5/08 607/2 |
| 2011/0264164 A1* | 10/2011 | Christopherson .... | A61B 5/4818 607/42 |

(Continued)

FOREIGN PATENT DOCUMENTS

WO  WO-2017/173331 A1  10/2017

OTHER PUBLICATIONS

International Search Report and Written Opinion on PCT/US2019/065792 dated Feb. 24, 2020. 13 pages.

(Continued)

*Primary Examiner* — Amanda K Hulbert
*Assistant Examiner* — Natasha Patel
(74) *Attorney, Agent, or Firm* — Foley & Lardner LLP (57) ABSTRACT

The present disclosure relates to a method for modulating the nervous system in order to reduce inflammation. The method includes delivering a vagus nerve stimulation (VNS) therapy to a vagus nerve of a patient for the treatment of inflammation according to a first set of parameters. The method further includes delivering a secondary nerve stimulation (SNS) therapy to a secondary nerve of the patient for the treatment of a sleep disorder according to a second set of parameters different from the first set of parameters.

20 Claims, 5 Drawing Sheets

(56) References Cited

U.S. PATENT DOCUMENTS

2016/0101289 A1* 4/2016 Stolen .............. A61N 1/36053
                                                    600/300
2018/0001077 A1* 1/2018 Cook ............... A61N 1/36031

OTHER PUBLICATIONS

Alberti, Andrea et al., "Plasma cytokine levels in patients with obstructive sleep apnea syndrome: a preliminary study;" 2003, European Sleep Research Society; J. Sleep Res., 12, pp. 305-311.

Ebben, Matthew et al., "Vagus Nerve Stimulation, Sleep Apnea, and CPAP Titration," Journal of Clinical Sleep Medicine, vol. 4, No. 5, 2008, pp. 471-473.

Egeberg, Alexander et al., "Psoriasis and Sleep Apnea: A Danish Nationwide Cohort Study," Journal of Clinical Sleep Medicine, vol. 12, No. 5, 2016, pp. 663-671.

Gabryelska, Agata et al., "Patients With Obstructive Sleep Apnea Are Over Four Times More Likely to Suffer From Psoriasis Than the General Population," Journal of Clinical Sleep Medicine, vol. 14, No. 1, p. 153.

Kheirandish-Gozal, Leila et al., "Obstructive Sleep Apnea and Inflammation: Proof of Concept Based on Two Illustrative Cytokines," International Journal of Molecular Sciences, 2019, vol. 20, No. 459, 19 pages.

Kinnucan, Jami et al., "Sleep and Inflammatory Bowel Disease: Exploring the Relationship Between Sleep Disturbances and Inflammation," Gastroenterology & Hepatology, vol. 9, Issue 11, Nov. 2013, pp. 718-727.

Kuna, Samuel, "Effects of Pharyngeal Muscle Activation on Airway Size and Configuration," Am J. Respir Crit Care Med, vol. 164, 2001, pp. 1236-1241.

Marzec, Mary et al., "Effects of Vagus Nerve Stimulation on Sleep-Related Breathing in Epilepsy Patients," Epilepsia, vol. 44, No. 7, 2003, pp. 930-935.

Vicente, Eugenio et al., "Upper Airway and Systemic Inflammation in Obstructive Sleep Apnoea," Eur Respir J., 2016, 48, pp. 1108-1117, DOI: 10.1183/13993003.00234-2016.

Wilton, Katelynn et al., "Risk of Obstructive Sleep Apnea and its Association with Cardiovascular and Non-Cardiac Vascular Risk in Patients With Rheumatoid Arthritis: A Population-Based Study," J. Rheumatol., Jan. 2018, vol. 45 No. 1, 15 pages, DOI: 10.3899/jrheum.170460.

Zambrelli, Elena et al., "Laryngeal Motility Alteration: A Missing Link Between Sleep Apnea and Vagus Nerve Stimulation for Epilepsy," Epilepsia, vol. 57, No. 1, pp. e-24-e-27, 2016, DOI: 10.1111/epi.13252.

* cited by examiner

NEUROMODULATION THERAPY FOR AUTO-IMMUNE AND INFLAMMATORY DISORDERS

CROSS-REFERENCE TO RELATED PATENT APPLICATION

This application claims the benefit of and priority to U.S. Provisional Patent Application No. 62/779,344, filed Dec. 13, 2018, which is hereby incorporated by reference in its entirety.

BACKGROUND

Auto-immune and other inflammatory disorders are often characterized by a variety of symptoms, including both localized inflammation as well as systemic inflammation. Often times, pharmaceuticals are used for the treatment of such diseases. However, patients often do not respond well or cannot tolerate the medication due to adverse side effects, the pharmaceuticals may only work for short periods of time before ceasing to provide any benefit. Thus an alternative method of treatment is necessary. While vagus nerve stimulation has been proposed as an alternative therapy to pharmaceuticals, there are still many unknowns in regards to stimulation for the purposes of treating chronic inflammatory and auto-immune diseases.

One of the main functions of the immune system is to protect the body against viruses, bacteria, and other invading microorganisms by producing antibodies which target and attack the invading microorganisms. In normal conditions, the immune response is not triggered against the cells of one's own body. However, when a person has an auto-immune disease, immune cells mistakenly attack the cells of their own body, damaging the body and causing a plurality of symptoms. Rheumatoid Arthritis (RA), Crohn's Disease, Ulcerative Colitis, Psoriasis, and Ankylosing Spondylitis are various types of auto-immune diseases, which present with a variety of similar symptoms. For example, RA is a form of arthritis which attacks the joints, causing symptoms such as joint pain, morning stiffness, and functional disability in the early morning hours. One of the underlying similarities between auto-immune diseases is chronic inflammation, which is also prominent in the symptomology and treatment goals for these diseases. Untreated inflammation can result in permanent damages, such as destruction of joints by RA. While the mechanisms are not completely understood, it is believed that the rise in inflammation is caused by a cascade phenomenon starting with a small population of activated immune cells, which signal more and more cells to become activated. This process has also been shown to be influenced by the autonomic nervous system. In particular, evidence suggests that an imbalance between activity in the sympathetic and parasympathetic branches of the autonomic nervous system may contribute to the disease process. Auto-immune diseases have often been treated with biological agents such as extrinsic monocolonal antibodies which attempt to reduce chronic inflammation by interfering with parts of the inflammatory cascade. However, the standard of care for managing auto-immune diseases in general continues to evolve. For instance, new therapeutic approaches that employ electrical stimulation of neural structures that directly address the underlying autonomic nervous system imbalance and inflammation have been proposed.

In both normal individuals and patients with immune-mediated inflammatory diseases (IMIDs), markers of inflammation follow consistent patterns throughout the day. In normal individuals, levels of Tumor Necrosis Factor (TNF) and Interleukin-6 (IL-6), both of which are cytokines associated with inflammation, reach a minimum in the morning after waking. These values then remain stable throughout most of the day, begin to rise in the early evening, and reach peak values in the early morning hours prior to waking. It has been discovered that this pattern is exaggerated in patients with IMIDs, with peak values significantly higher than normal. Thus, the inflammation caused by IMIDs is cyclical, occurring based on a patient's natural Circadian rhythm.

While modulation via electrical stimulation of various nerves has been proposed as an anti-inflammatory therapy, the most prominent proponents of such an approach advocate for vagus nerve stimulation (VNS). Specifically, VNS has been proposed as a method of affecting the cholinergic anti-inflammatory reflex. The proposed mechanism of this reflex has recently been refined to take account of the fact that the spleen is not directly innervated by the vagus nerve, but rather the splenic (sympathetic) nerve. Because an imbalance in intrinsic autonomic activity is thought to be part of the disease process, an intervention is required to drive the system back towards equilibrium. Thus, there is a need for a system to modulate inflammatory behavior by simulation of both peripheral nerves as well as the central nervous system, and particularly based on Circadian rhythm and the sleep state of the patient.

Current neurostimulation systems used for treatment of inflammatory disorders do not sense or record information relevant to patient status. Conventional biomarkers of inflammation, such as C-Reactive Protein, IL-6, and Fibrinogen, have been shown to correlate with heart rate (HR), indicating that the measurement of HR could be particularly insightful regarding patient status. Additionally, environmental factors may have a significant impact on inflammation through physiologic functions, including respiration and digestion. Thus, a need remains for a system that monitors patient status and environmental factors surrounding the patient to better (responsively) treat chronic inflammation. Additionally, cardiovascular disease is also known to correlate with IMIDs and may indeed be an IMID itself. For example, a higher prevalence of cardiovascular disease is responsible for excess mortality in patients with IMIDs. Stimulation of the carotid sinus nerve has been shown to both reduce blood pressure, and to improve symptoms of heart failure in association with increased efferent vagus (parasympathetic) and decreased sympathetic nerve activity, which are two of the processes by which VNS is believed to reduce inflammation. Additionally, it has recently been found that sleep quality is linked to inflammation, both of which may be precursors of cardiovascular disease. Sleep quality issues, such as movement or interruption of sleep, insufficient sleep hours, inconsistent sleep schedules, inadequate amount of time spent in particular sleep stages, or excessive sleep, has been linked to higher risks of inflammation, and vice versa. A combined therapy device for stimulation of multiple locations, such as the vagus nerve and carotid sinus nerve, may be beneficial for the treatment of both inflammation due to IMIDs, sleep quality issues, as well as symptoms of cardiovascular disease by providing reinforcing dual extrinsic modulation of autonomic tone.

Thus, it would be advantageous to have systems and methods for delivering nerve stimulation via a plurality of nerves to patients for treating chronic inflammation and/or auto-immune disease. Systems and methods are provided for delivering nerve stimulation via a plurality of nerves to patients for treating chronic inflammation and/or auto-immune diseases.

SUMMARY

Systems and methods are provided for neuromodulation via electrical stimulation and, more specifically, to improved systems and methods for delivering stimulation for the treatment of auto-immune/inflammatory disorders. The electrical stimulation may be provided to multiple sites or at multiple stimulation levels using an implantable pulse generator.

One implementation of the present disclosure is a method for modulating the nervous system in order to reduce inflammation. The method includes delivering a vagus nerve stimulation (VNS) therapy to a vagus nerve of a patient for the treatment of inflammation according to a first set of parameters. The method further includes delivering a secondary nerve stimulation (SNS) therapy to a secondary nerve of the patient for the treatment of a sleep disorder according to a second set of parameters different from the first set of parameters.

Another implementation of the present disclosure is a system for modulating the nervous system to reduce inflammation. The system includes a pulse a pulse generator configured to generate pulsed electrical signals, a lead, one or more electrodes communicatively coupled to the pulse generator via the lead, wherein the pulse generator is configured to apply the pulsed electrical signal to one or more nerves via the one or more electrodes, and a processor. The processor is configured to deliver a vagus nerve stimulation (VNS) therapy to a vagus nerve of a patient for the treatment of inflammation via the one or more electrodes according to a first set of parameters, and deliver a secondary nerve stimulation (SNS) therapy to a secondary nerve of the patient for the treatment of a sleep disorder via the one or more electrodes according to a second set of parameters different from the first set of parameters.

Another implementation of the present disclosure is a non-transitory computer-readable medium having instructions stored thereon that are executable by a processor of an implantable neurostimulation system to cause the processor to perform operations comprising delivering a vagus nerve stimulation (VNS) therapy to a vagus nerve of a patient for the treatment of inflammation according to a first set of parameters. The operations further comprise delivering a secondary nerve stimulation (SNS) therapy to a secondary nerve of the patient for the treatment of a sleep disorder according to a second set of parameters different from the first set of parameters.

Those skilled in the art will appreciate this summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE DRAWINGS

Further features, characteristics and advantages of the present disclosure will become apparent to a person of ordinary skill in the art from the following detailed description of preferred embodiments of the present disclosure, made with reference to the drawings annexed, in which like reference characters refer to like elements, and in which.

DETAILED DESCRIPTION

Various aspects of the disclosure will now be described with regard to certain examples and embodiments, which are intended to illustrate but not to limit the disclosure. Nothing in this disclosure is intended to imply that any particular feature or characteristic of the disclosed embodiments is essential. The scope of protection is defined by the claims that follow this description and not by any particular embodiment described herein. Before turning to the figures, which illustrate example embodiments in detail, it should be understood that the application is not limited to the details or methodology set forth in the description or illustrated in the figures. It should also be understood that the terminology is for the purpose of description only and should not be regarded as limiting.

VNS has been proposed and tested as a treatment for chronic inflammation due to auto-immune disorders. However, the efficacy of VNS may vary from patient to patient, such that VNS may positively affect some patients while minimally affecting other patients. In some embodiments of the present disclosure, nerve stimulation for the treatment of chronic inflammation may be improved by multi-site stimulation, such as stimulation of the vagus nerve in addition to the carotid sinus nerve (or other peripheral nerve(s)). Further, some embodiments of the disclosure identify methods for monitoring patient characteristics via a plurality of sensors to deliver efficient stimulation to each and every patient. In some embodiments, the plurality of sensors may monitor the sleep quality of the patient, which has been linked to inflammation, and stimulation may be delivered in order to target both improved sleep quality and reduction in inflammation. Further, in some embodiments of the disclosure, nerve stimulation may be improved by delivering stimulation based on Circadian rhythms of a patient. Finally, in some embodiments of the present disclosure, nerve simulation may be improved by delivering stimulation aimed at treating both cardiovascular disease as well as inflammation caused by auto-immune diseases.

Referring to the Figures generally, the present disclosure relates to apparatuses, systems, and methods for treating patients with chronic inflammation and other symptoms caused by a plurality of IMIDs. Some IMIDs, such as RA, are often characterized by persistent synovial inflammation, which may lead to joint deformity, stiffness, and bone erosion. Other IMIDs, such as Crohn's Disease, also feature persistent inflammation, but in other areas such as the alimentary canal in the intestines. Likewise, psoriasis is characterized by persistent inflammation of the skin. The cause of IMIDs varies slightly based on the specific disease, but there are similar characteristics throughout IMIDs. For example, in patients with RA, inflammation has been linked to certain alleles of the major histocompatibility complex. One such example are the $CD_4$ T cells, which are regulators of the immune response secreting pro-inflammatory cytokines, such as TNF and IL-6. In patients with RA, a feedback mechanism of the cytokines trigger angiogenesis, which establishes a feedback loop that favors continuous leukocyte infiltration and chronic inflammation.

The prevalence of IMIDs is widespread, affecting approximately 5% of the population worldwide. Despite numerous pharmaceuticals available for the treatment of IMIDs, patients often become refractory to medication. The general belief among physicians is that the long-term rate control of IMIDs using pharmaceuticals is approximately 30-40%. Thus, the majority of patients are not controlled in the long term using last-line medical therapies. Additionally, the side effects of biologic drugs are also significant, including reducing resistance to infection (immunosuppression) and risk of cancer. Likewise, compliance is an issue, as traditional biologic drugs require periodic self-injection or regular visits to an infusion center. Doses are often separated by weeks, such that they are only capabale of globally suppressing the patterns of inflammation rather than having a significant influence on circadian patterns of inflammation. Thus, there is a need for an alternative method of treatment that targets the physiological aspects of IMIDs in a low-risk manner. While the vagus nerve plays an important role in modulating inflammation, other nerves, both afferent and efferent, have also been shown to exert profound influences on inflammation. Thus, a system which selectively modulates key portions of both efferent and afferent pathways may be especially effective at treating IMIDs.

An implantable nerve stimulator, such as a vagus nerve stimulator used to treat drug-refractory epilepsy and depression, can be adapted for use in managing chronic inflammation through therapeutic nerve stimulation. Stimulation may be directly and/or indirectly applied to the vagus nerve (cervical or abdominal), the carotid sinus nerve, the aortic depressor nerve, the greater splanchnic nerve, the splenic nerve, the trigeminal nerve, paravertebral ganglia associated with sympathetic nerves, local sympathetic nerve near the site of inflammation, or any combination thereof. Additionally, simulation may be selective to certain fibers of the vagus nerve In some embodiments, the nerve stimulator may comprise multiple leads with multiple electrodes aimed at targeting two or more nerves. In other embodiments, multiple nerve stimulators may be used, each nerve stimulator aimed to target a nerve (in some embodiments there would be communication/coordination between/among the various stimulators). A vagus nerve stimulation (VNS) system will now be described in detail, as an exemplary embodiment of a system for stimulation. Similar systems may be used to target any of the variety of additional nerves disclosed herein.

The vagus nerve is a diverse nerve trunk that contains both sympathetic and parasympathetic fibers, and both afferent and efferent fibers. These fibers have different diameters and degrees of myelination, and subsequently have different activation thresholds. This results in a graded response as intensity is increased. Low intensity stimulation results in a progressively greater tachycardia, which then diminishes and is replaced with a progressively greater bradycardia response as intensity is further increased. Peripheral neurostimulation therapies that target the fluctuations of the autonomic nervous system have been shown to improve clinical outcomes in some patients. Specifically, autonomic regulation via VNS results in simultaneous creation and propagation of efferent and afferent action potentials within nerve fibers comprising the cervical vagus nerve. The therapy directly improves autonomic balance by engaging both medullary and cardiovascular reflex control components of the autonomic nervous system. Upon stimulation of the cervical vagus nerve, action potentials propagate away from the stimulation site in two directions, efferently toward the heart and afferently toward the brain. Efferent action potentials influence the intrinsic cardiac nervous system and the heart and other organ systems, while afferent action potentials influence central elements of the nervous system. Afferent fibers from the vagus nerve reach most of the major internal organs such as the stomach, intestines, lungs, etc.

Figure 1:
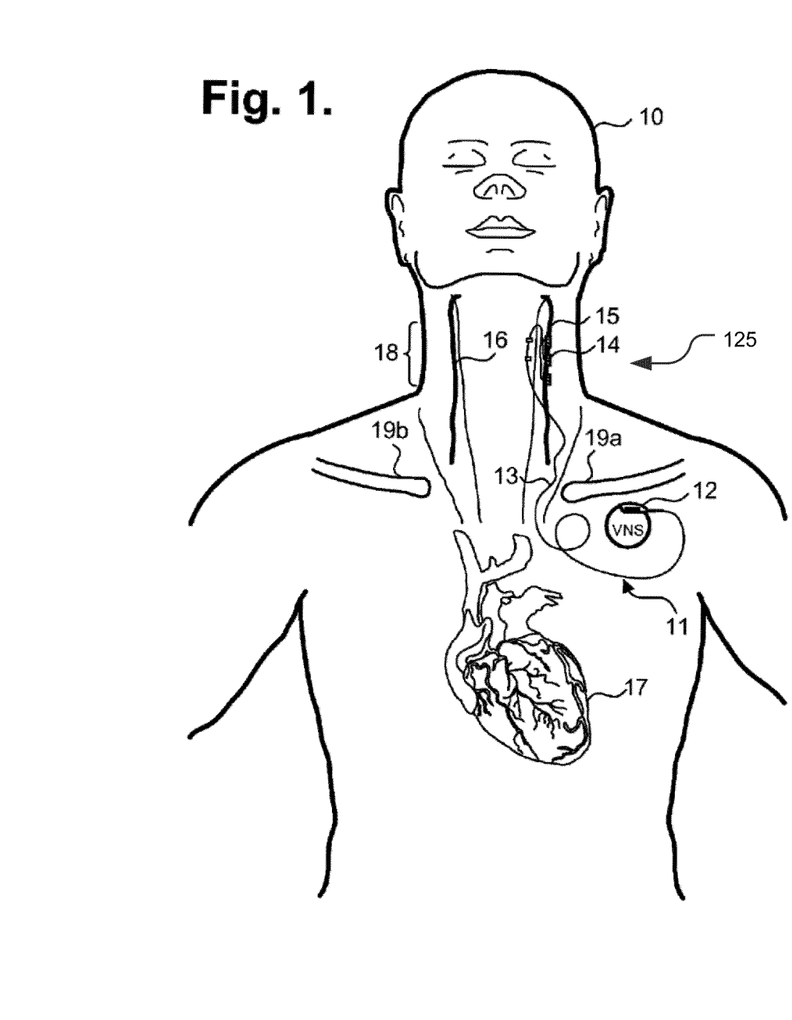
FIG. 1 is a front anatomical diagram showing, by way of example, placement of an implantable vagus stimulation device in a male patient, according to an exemplary embodiment.

An implantable vagus nerve stimulator, such as used to treat drug-refractory epilepsy and depression, can be adapted for use in managing chronic inflammation caused by IMIDs through therapeutic bi-directional vagus nerve stimulation. FIG. 1 is a front anatomical diagram showing, by way of example, placement of an implantable medical device (e.g., a vagus nerve stimulation (VNS) system 11, as shown in FIG. 1) in a male patient 10, in accordance with an embodiment of the present invention. The VNS provided through the stimulation system 11 operates under several mechanisms of action. These mechanisms include increasing parasympathetic outflow and inhibiting sympathetic effects by inhibiting norepinephrine release and adrenergic receptor activation. More importantly, VNS triggers the release of the endogenous neurotransmitter acetylcholine and other peptidergic substances into the synaptic cleft, which has several beneficial anti-inflammatory effects as well as beneficial effects at the level of the central nervous system. Central effects of VNS may also directly alter sympathetic outflow, as has been shown in animal models of acute inflammation.

The implantable vagus stimulation system 11 comprises an implantable neurostimulator or pulse generator 12 and a stimulating nerve electrode assembly 125. The stimulating nerve electrode assembly 125, preferably comprising at least an electrode pair, is conductively connected to the distal end of an insulated, electrically conductive lead assembly 13 and electrodes 14. The electrodes 14 may be provided in a variety of forms, such as, e.g., helical electrodes, probe electrodes, cuff electrodes, as well as other types of electrodes.

The neurostimulator 12 is typically implanted in the patient's right or left pectoral region generally on the same side (ipsilateral) as the vagus nerve 15, 16 to be stimulated, although other neurostimulator-vagus nerve configurations, including contra-lateral and bi-lateral are possible. A vagus nerve typically comprises two branches that extend from the brain stem respectively down the left side and right side of the patient, as seen in FIG. 1. The electrodes 14 are generally implanted on the vagus nerve 15, 16 about halfway between the clavicle 19a-b and the mastoid process. The electrodes may be implanted on either the left or right side. The lead assembly 13 and electrodes 14 are implanted by first exposing the carotid sheath and chosen branch of the vagus nerve 15, 16 through a latero-cervical incision (perpendicular to the long axis of the spine) on the ipsilateral side of the patient's neck 18. The helical electrodes 14 are then placed onto the exposed nerve sheath and tethered. A subcutaneous tunnel is formed between the respective implantation sites of the neurostimulator 12 and helical electrodes 14, through which the lead assembly 13 is guided to the neurostimulator 12 and securely connected. In other embodiments, the neurostimulator 12 may be implanted endoscopically, based on the observation that many potential nerve stimulation targets are within reach of the esophagus, stomach, and gut. Existing endoscopic ultrasound systems used in interventional endoscopy procedures can image some of these disclosed nerves at the present time. Such systems may be used to implant electrodes or microstimulation devices to target various nerves, as previously described.

In one embodiment, the neural stimulation is provided as a low level dose independent of cardiac cycle. The stimulation system 11 bi-directionally stimulates either the left vagus nerve 15 or the right vagus nerve 16. However, it is contemplated that multiple electrodes 14 and multiple leads 13 could be utilized to stimulate simultaneously, alternatively or in other various combinations. Stimulation may be through multimodal application of continuously-cycling, intermittent and periodic electrical stimuli, which are parametrically defined through stored stimulation parameters and timing cycles. Both sympathetic and parasympathetic nerve fibers in the vagosympathetic complex are stimulated.

Figure 2A:
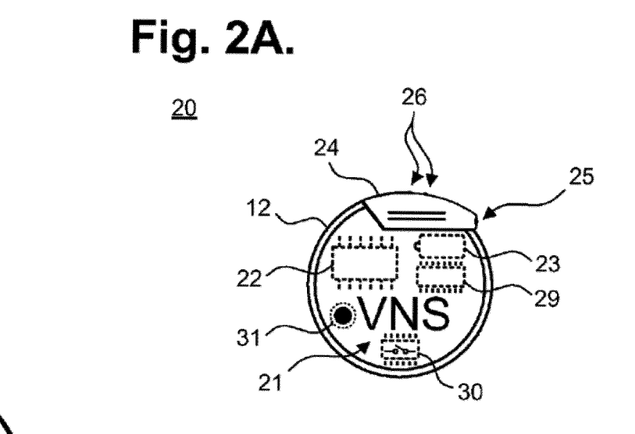
FIGS. 2A and 2B are diagrams respectively showing the implantable neurostimulator and the stimulation therapy lead of FIG. 1, according to an exemplary embodiment.
Figure 2B:
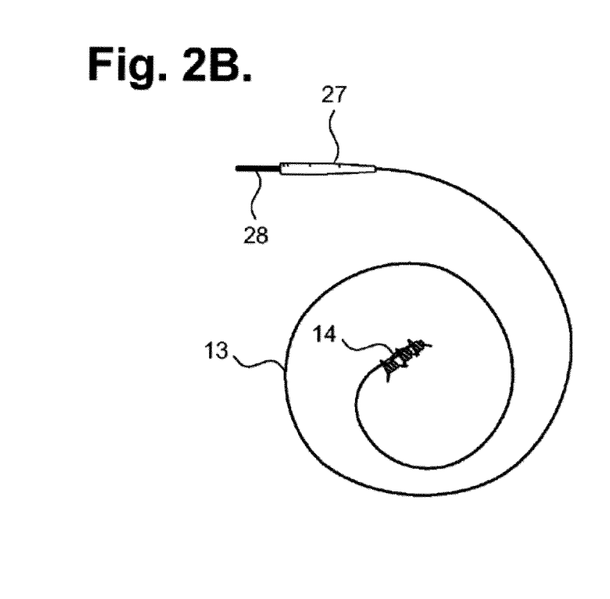

The VNS therapy is delivered autonomously to the patient's vagus nerve 15, 16 through three implanted components that include a neurostimulator 12, lead assembly 13, and electrodes 14. FIGS. 2A and 2B are diagrams respectively showing the implantable neurostimulator 12 and the stimulation lead assembly 13 of FIG. 1. In one embodiment, the neurostimulator 12 can be adapted from a VNS Therapy Demipulse Model 103 or AspireSR Model 106 pulse generator, manufactured and sold by Cyberonics, Inc., Houston, Tex., although other manufactures and types of implantable VNS neurostimulators could also be used. The stimulation lead assembly 13 and electrodes 14 are generally fabricated as a combined assembly and can be adapted from a Model 302 lead, PerenniaDURA Model 303 lead, or PerenniaFLEX Model 304 lead, also manufactured and sold by Cyberonics, Inc., in two sizes based, for example, on a helical electrode inner diameter, although other manufactures and types of single-pin receptacle-compatible therapy leads and electrodes could also be used.

Referring first to FIG. 2A, the system 20 may be configured to provide multimodal vagus nerve stimulation. In a low-level mode, the neurostimulator 12 is parametrically programmed to deliver continuously-cycling, intermittent and periodic ON-OFF cycles of VNS. Such delivery produces action potentials in the underlying nerves that propagate bi-directionally, both afferently and efferently, in some nerve systems. However, other nerve systems, such as the splenic nerve, contains only efferent sympathetic nerve fibers. While stimulation would also generate bidirectional action potentials, the current understanding of physiology would imply that in nerves such as the splenic nerve there would be no effect of the afferent action potential, as there are no afferent sympathetic nerve fibers.

The neurostimulator 12 includes an electrical pulse generator that is tuned to improve autonomic regulatory function by triggering action potentials that propagate both afferently and efferently within the vagus nerve 15, 16. The neurostimulator 12 is enclosed in a hermetically sealed housing 21 constructed of a biocompatible material, such as titanium. The housing 21 contains electronic circuitry 22 powered by a battery 23, such as a lithium carbon monofluoride primary battery or a rechargeable secondary cell battery. The electronic circuitry 22 may be implemented using complementary metal oxide semiconductor integrated circuits that include a microprocessor controller that executes a control program according to stored stimulation parameters and timing cycles; a voltage regulator that regulates system power; logic and control circuitry, including a recordable memory 29 within which the stimulation parameters are stored, that controls overall pulse generator function, receives and implements programming commands from the external programmer, or other external source, collects and stores telemetry information, processes sensory input, and controls scheduled and sensory-based therapy outputs; a transceiver that remotely communicates with the external programmer using radio frequency signals; an antenna, which receives programming instructions and transmits the telemetry information to the external programmer; and a reed switch 30 that provides remote access to the operation of the neurostimulator 12 using an external programmer, a simple patient magnet, or an electromagnetic controller. The recordable memory 29 can include both volatile (dynamic) and non-volatile/persistent (static) forms of memory, such as firmware within which the stimulation parameters and timing cycles can be stored. Other electronic circuitry and components are possible.

The neurostimulator 12 includes a header 24 to securely receive and connect to the lead assembly 13. In one embodiment, the header 24 encloses a receptacle 25 into which a single pin for the lead assembly 13 can be received, although two or more receptacles could also be provided, along with the corresponding electronic circuitry 22. The header 24 internally includes a lead connector block (not shown) and a set of screws 26.

In some embodiments, the housing 21 may also contain a sensor 31 that is electrically interfaced with the logic and control circuitry. In some embodiments, the sensor 31 may be a heart rate sensor, which receives the patient's sensed heart rate as sensory inputs. The sensor 31 may monitor heart rate using an ECG-type electrode. Through the electrode, the patient's heart beat can be sensed by detecting ventricular depolarization. In a further embodiment, a plurality of electrodes can be used to sense voltage differentials between electrode pairs, which can undergo signal processing for cardiac physiological measures, for instance, detection of the P-wave, QRS complex, and T-wave. The sensor 31 provides the sensed heart rate to the control and logic circuitry as sensory inputs that can be used to determine the onset or presence of arrhythmias, particularly VT, and/or to monitor and record changes in the patient's heart rate over time or in response to applied stimulation signals.

In other embodiments, the sensor 31 may be a minute ventilation sensor used to determine patient awakening. Minute ventilation is closely tied to heart rate during sleep, as ventilatory volume (tidal volume) and breathing frequency (respiratory rate) decrease synchronously, as does heart rate, as the patient falls asleep, then settles into a regular pattern. Tidal volume at rest may be measured by the sensor 31. In general, tidal volume at rest is around 0.5 L/min and can increase up to 3 L/min at a higher intensity level of exertion. Similarly, respiratory rate at rest is measured by the sensor 31. In general, respiratory rate at rest is around 12 to 16 breathes/min and can increase 40 to 50 breathes/min during maximum levels of activity. A normative activity level while asleep is established by determining means of the tidal volume and respiratory rate. If tidal volume and respiratory rate of the patient 10 respectively exceed the mean resting values of tidal volume and respiratory rate, the patient 10 is considered to be awakening. Still other measures and indications of awakening are possible.

In other embodiments, the sensor 31 may be an accelerometer that is electrically interfaced with the logic and control circuitry, which receives the patient's physical movement as sensory inputs. The sensor 31 may contain the circuitry and mechanical components necessary to measure acceleration of the patient's body along at least two axes, and may include multiple uniaxial accelerometers, a dual axial accelerometer, or a triaxial accelerometer. By measuring the acceleration along multiple axes, the sensor 31 provides sensory inputs that can be used to determine the patient's posture, such as if the patient is standing or lying down, and rate of movement and whether the patient has fallen or awakened from sleep. In other embodiments, the neurostimulator may contain multiple sensors 31, including any combination of a heart rate sensor, a minute ventilation sensor, an accelerometer, or any other sensor used to gather patient information.

Referring next to FIG. 2B, the lead assembly 13 delivers an electrical signal from the neurostimulator 12 to the vagus nerve 15, 16 via the electrodes 14. On a proximal end, the lead assembly 13 has a lead connector 27 that transitions an insulated electrical lead body to a metal connector pin 28. During implantation, the connector pin 28 is guided through the receptacle 25 into the header 24 and securely fastened in place using the set screws 26 to electrically couple the lead assembly 13 to the neurostimulator 12. On a distal end, the lead assembly 13 terminates with the electrode 14. In one embodiment, the lead connector 27 is manufactured using silicone and the connector pin 28 is made of stainless steel, although other suitable materials could be used, as well. The insulated lead body 13 utilizes a silicone-insulated alloy conductor material.

In some embodiments, the electrodes 14 are helical and placed around the cervical vagus nerve 15, 16 at the location below where the superior and inferior cardiac branches separate from the cervical vagus nerve. In alternative embodiments, the helical electrodes may be placed at a location above where one or both of the superior and inferior cardiac branches separate from the cervical vagus nerve. In some embodiments, the helical electrodes may be placed at locations closer to the gut, for example at the hepatic branch of the vagus nerve. In one embodiment, the helical electrodes 14 are positioned around the patient's vagus nerve oriented with the end of the helical electrodes 14 facing the patient's head. In an alternate embodiment, the helical electrodes 14 are positioned around the patient's vagus nerve 15, 16 oriented with the end of the helical electrodes 14 facing the patient's heart 17. At the distal end, the insulated electrical lead body 13 is bifurcated into a pair of lead bodies that are connected to a pair of electrodes. The polarity of the electrodes could be configured into a monopolar cathode, a proximal anode and a distal cathode, or a proximal cathode and a distal anode.

In some embodiments, the neurostimulator may be interrogated prior to implantation and throughout the therapeutic period with a healthcare provider-operable control system comprising an external programmer and programming wand (not shown) for checking proper operation, downloading recorded data, diagnosing problems, and programming operational parameters, such as described in commonly assigned U.S. Pat. No. 8,600,505, entitled "Implantable Device For Facilitating Control Of Electrical Stimulation Of Cervical Vagus Nerves For Treatment Of Chronic Cardiac Dysfunction," the disclosure of which is incorporated by reference. The external programmer may include a healthcare provider operable programming computer and a programming wand, and use of the programmer may be restricted to healthcare providers, while more limited manual control may be provided to the patient through various modes.

Figure 3:
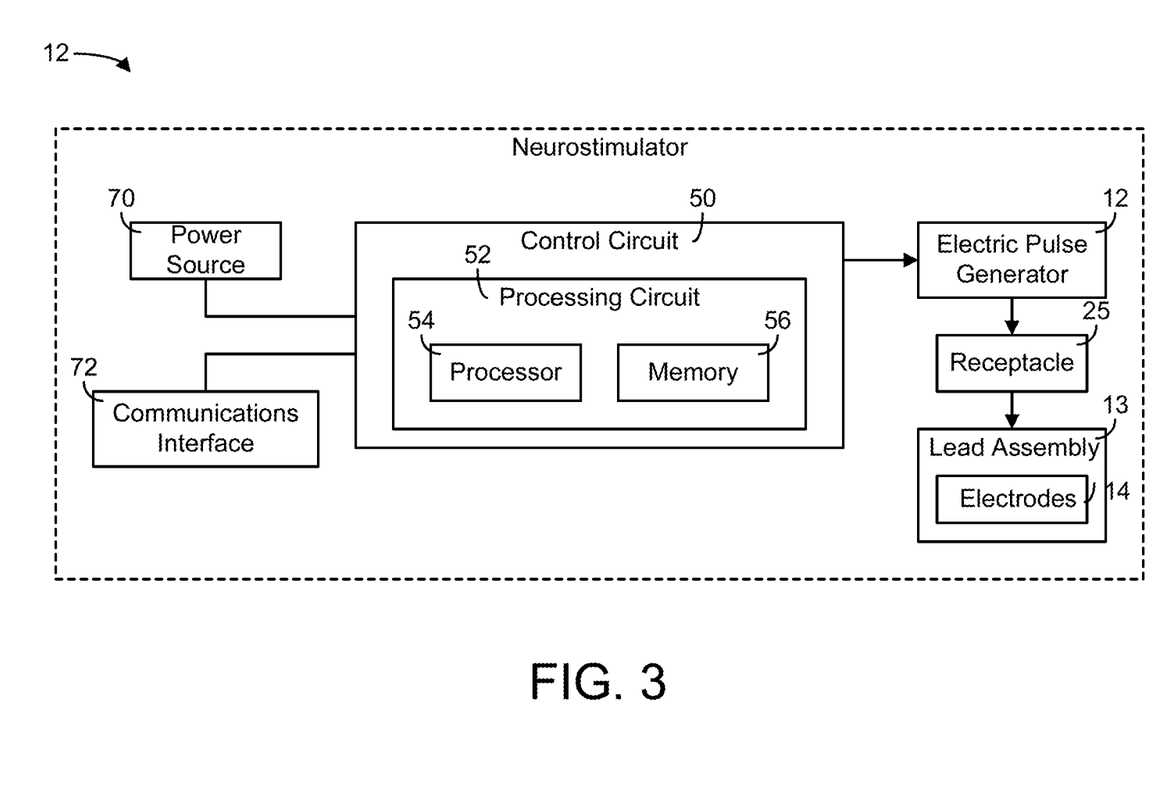
FIG. 3 is a schematic block diagram of the nerve stimulation device of FIG. 1, according to an exemplary embodiment.

As shown in FIG. 3, a control circuit 50 of the neurostimulator 12 includes a processing circuit 52. The processing circuit 52 includes a processor 54 and a memory 56. The processor 54 may be implemented as a general-purpose processor, a micro-processor, an application specific integrated circuit (ASIC), one or more field programmable gate arrays (FPGAs), a digital signal processor (DSP), a group of processing components, or other suitable electronic processing components. The memory 56 (e.g., RAM, ROM, Flash Memory, hard disk storage, etc.) may store data and/or computer code for facilitating the various processes described herein. Thus, the memory 56 may be communicably connected to the processor 54 and provide computer code or instructions to the processor 54 for executing the processes described in regard to the vagus nerve stimulator 10 herein. Moreover, the memory 56 may be or include tangible, non-transient volatile memory or non-volatile memory. In some embodiments, the memory 56 may include database components, object code components, script components, or any other type of information structure for supporting the various activities and information structures described herein.

The memory 56 may include various modules for completing processes described herein. More particularly, the memory 56 includes modules configured to control operation of the vagus nerve stimulator 10 to provide ART via VNS and/or eVNS. The memory 56 may store a control program that operates the vagus nerve stimulator 10 according to stored stimulation parameters and timing cycles (e.g., a predefined stimulation protocol, etc.). For example, the memory 56 may include a voltage module that regulates system power, a stimulation module that controls the overall pulse generator function, an input module that receives and implements programming commands from the external programmer or other external source, and/or data module that collects and stores telemetry information, among other possible modules that perform additional or alternative functions. While various modules with particular functionality may be used, it will be understood that the memory 56 may include any number of modules for completing the functions described herein. For example, the activities of multiple modules may be combined as a single module and additional modules with additional functionality may be included. Further, it will be understood that the processing circuit 52 of the neurostimulator 12 may further control other processes beyond the scope of the present disclosure.

In some embodiments of the present invention, neurostimulation may be delivered to the patient 100 based on their circadian rhythm. In some embodiments, input from the sensor 31 may be used to determine a sleep stage of the patient, such as activity measured by an accelerometer, the patient's heart rate, core body temperature, intrinsic central or peripheral nerve activity, or any combination of input thereof. Further, the time of day may be programmed into the memory 56 of neurostimulator 12, and neurostimulator may automatically modify simulation based on the known time of day, regardless of input from the sensor 31. In other embodiments, the sleep stage of the patient may be determined based on a combination of input from the sensor 31 as well as the known time of day. The stimulation delivered by neurostimulator 12 may be provided to any variety of nerves, including but not limited to the vagus nerve, the carotid sinus nerve, the aortic depressor nerve, the greater splanchnic nerve, and the splenic nerve, or any combination thereof. In some embodiments, the neurostimulator 12 may be configured to stimulate different nerves based on the time of day or the sleep stage of the patient determined by input from the sensor 31.

Figure 4:
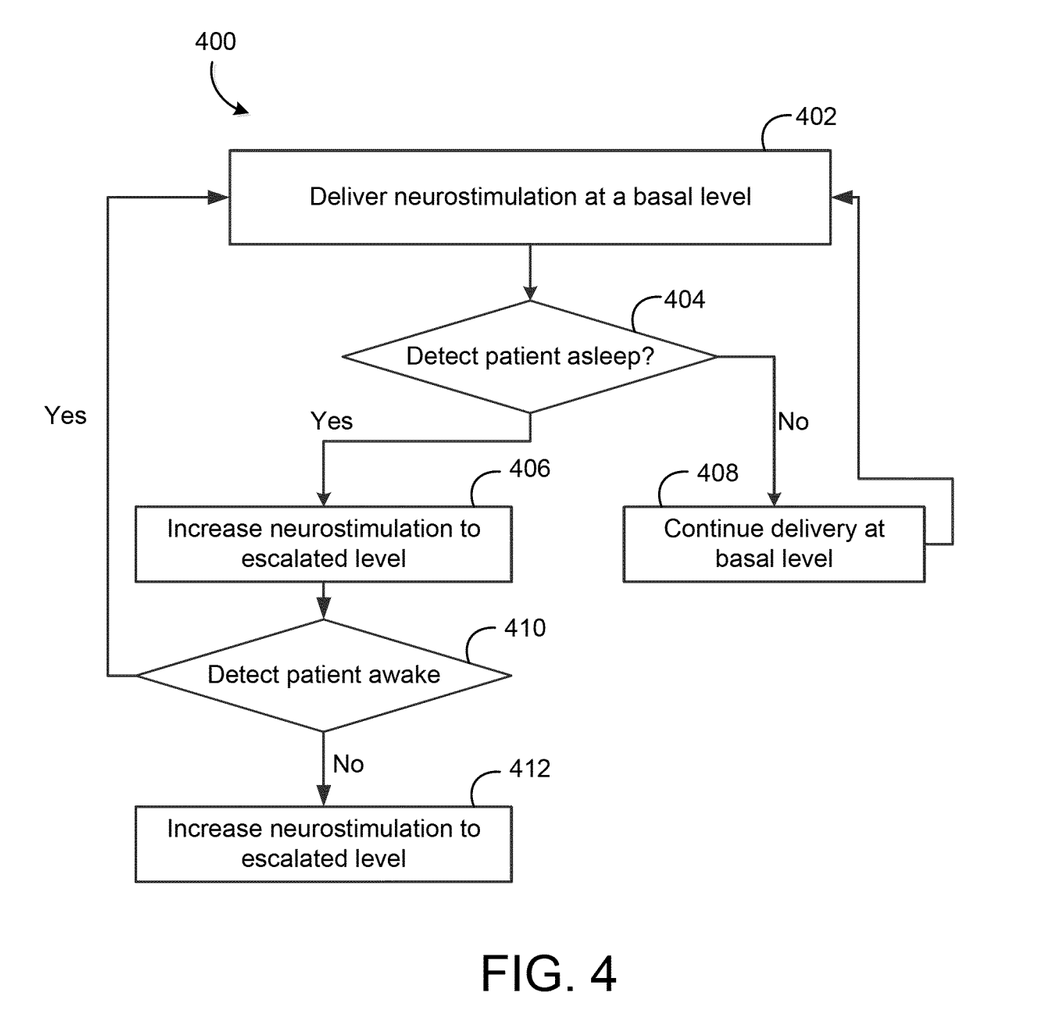
FIG. 4 illustrates a method for modifying the delivery of neurostimulation, according to an exemplary embodiment.

FIG. 4 illustrates a method 400 for delivering stimulation based on circadian rhythm, in accordance with embodiments of the present invention. The level of cytokines varies with circadian rhythm, thus in order to optimally deliver neurostimulation to treat inflammation, it is beneficial to deliver stimulation according to circadian rhythm. Additionally, determining the circadian rhythm allows the stimulation to be modified based on whether or not the patient is in an asleep or an awake state. If in the asleep state, the patient may have sleep quality issues, as described in further detail below, and stimulation may further be delivered to improve sleep quality of the patient.

In some embodiments, the method 400 may be executed by the processor 54 of neurostimulator 12. At step 402, the neurostimulator 12 delivers therapy in accordance with any desired stimulation therapeutic modality, as described herein. The neurostimulator 12 beings to deliver therapy at a basal level. A basal level may correspond to a low level of stimulation. The basal level may be predetermined and stored in memory 56 or may be determined on a patient to patient basis, for example, by input from the sensor 31. At decision step 404, the processor 54 determines if the patient 100 is asleep. The sleep stage of the patient 100 may be determined by inputs received from the sensor 31, or simply by the known time of day. If it is detected that the patient 100 is awake at step 408, the stimulation level remains at the basal level and the process returns to step 402.

If, however, it is detected that the patient 100 is asleep, at step 406, the stimulation level is progressively increased to an escalated level. In some embodiments, the detection of sleep of the patient is based on timing relative to when the patient is expected to be asleep for the day, e.g. sleep history, the time of day, data received from the sensor 31, or patient input. In some embodiments, the stimulation level may be increased as a step-change response, based on the sleep stage of the patient (e.g., I, II, III, or IV). In other embodiments, the stimulation level may be modified on a more gradual level, such that the stimulation increase occurs gradually once sleep is detected. The increase of stimulation level involves the modification of neurostimulation dose, which may include modifying one or more of the amplitude, frequency, pulse width, duty cycle, polarity, and number of active sites of stimulation. At step 410, the processor 54 determines if the patient 100 is awake. If it is detected that the patient is awake, the stimulation decreases back to a basal level and returns to step 402. In some embodiments, the detection of wakefulness of the patient is based on timing relative to when the patient is expected to be awake for the day, e.g. sleep history, the time of day, data received from the sensor 31, or patient input. The neurostimulation level may decrease as a step-change response is response to a level of wakefulness of the patient 100, which may be determined by input from the sensor 31 or known time of day. In other embodiments, the stimulation level may be modified on a more gradual level, such that the stimulation decrease occurs gradually once wakefulness is detected. However, if it is determined that the patient 100 is not awake, stimulation is maintained at the escalated level at step 412.

In some embodiments, each patient may have their own individualized profile corresponding to the level of stimulation with a personalized treatment plan based on their own individual day and night cycle. In other embodiments, the patients 100 inflammation may be monitored based on their circadian rhythm to determine the appropriate levels of stimulation. In some embodiments, the sleep state of the patient may be used in conjunction with the methods described below in order to determine appropriate levels of stimulation for both IMID's and various other conditions.

Figure 5:
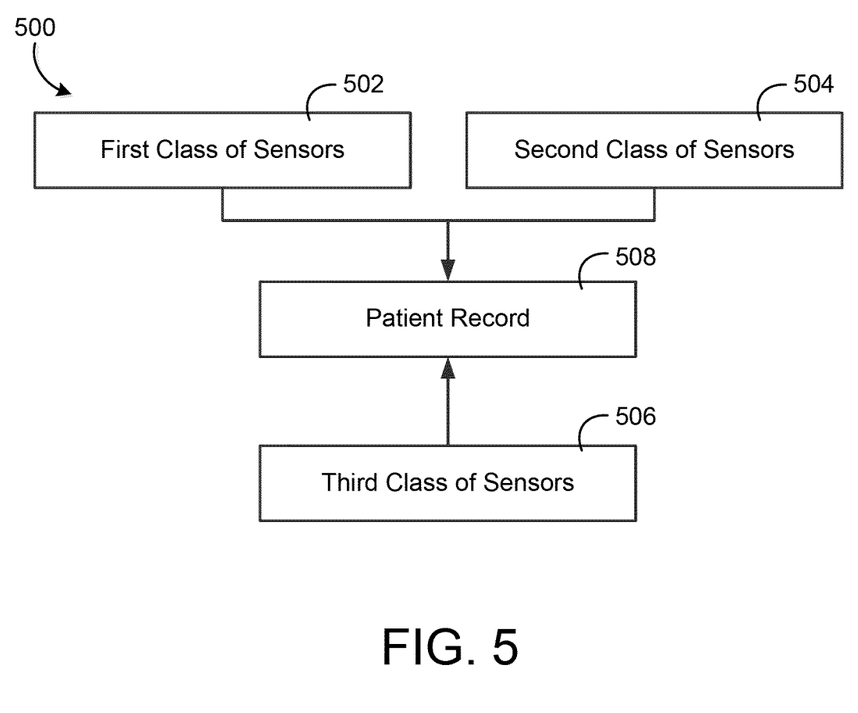
FIG. 5 is a schematic block diagram of a system for modifying the delivery of neurostimulation, according to an exemplary embodiment.

In some embodiments of the present invention, a plurality of sensors may be used to determine the necessary characteristics of neurostimulation in order to best ameliorate chronic inflammation by modulating the neurostimulator 12. In some embodiments, neurostimulator 12 may be used in conjunction with the data received from the three different classes of sensors in order to optimize the therapy in a patient record 508, as seen in FIG. 5. FIG. 5 generally shows a system 500 modifying the delivery of neurostimulation based on the feedback received from various sensors, according to an exemplary embodiment. The patient record may receive input from a first class of sensors 502, a second class of sensors 504, and a third class of sensors 506, to assess the patient's condition and collect long term data regarding the patient's inflammation based on a variety of factors.

The first class of sensors 502 may be used to collect physiological data from the patient. In some embodiments, the first class of sensors 502 may include sensor 31. The first class of sensors 502 may contain multiple sensors, including any combination of a heart rate sensor, a minute ventilation sensor, an accelerometer, a body core temperature sensor, or any other sensor used to gather patient information. In some embodiments, physiological data from the patient may correspond with biomarkers of inflammation, such as C-Reactive Protein, IL-6, and Fibrinogen, all of which have been shown to correlate with heart rate. In other embodiments, physiological data from the patient may correspond with patient activity level, such as may be determined by an accelerometer. The first class of sensors 502 may be incorporated into neurostimulator 12, which is used to treat inflammatory disease, in order to collect real time physiological data from the patient. In some embodiments, the first class of sensors 502 may be used to detect a level of inflammation of the patient, and further may flag an alert on the patient record 508 if the level of inflammation becomes too high. For example, it is well known that there is a correlation between heart rate and inflammation. If it is determined that there is a reduction in patient activity with an increase in heart rate, the first class of sensors 502 may alert the patient record 508, which is accessible by a physician, so that appropriate steps may be taken to control the inflammation. The patterns of variation in heart rate, determined by the first class of sensors 502, may also contain useful information, regarding inflammation and other symptoms. In still other embodiments, a body core temperature sensor as part of the first class of sensors 502 may detect a rise in body temperature, which may indicate that an infection has occurred. Stimulation may be modified accordingly in order to ward off the infection.

The second class of sensors 504 may be used to collect environmental data based on a patient's surroundings. The environment significantly influences inflammation through physiologic functions including respiration and digestion, which may include particulate matter, gasses, and other pollution that may enter the body and cause an increase in inflammation. In some embodiments, the second class of sensors 504 may include an external sensor, which may be worn by the patient, and may track one or more of these pollutants. In other embodiments, the second class of sensors 504 may include a sensor configured to detect environmental conditions, such as temperature, humidity, or sunlight exposure in the patient's surroundings, or may further include a geographical tracker which tracks a patient's general location in order to import information relating to environmental conditions. It is believed that some of the seasonal increases in IMIDs that occur in the winter may be due to reduced sunlight exposure due to the change in Vitamin D synthesis. In still other embodiments, the second class of sensors 504 may include a patient diet tracker system, in which the system may track self-reported food intake of or semi-automated logging of ingestion. The second class of sensors 504 may provide any combination of information collected by the sensors to the patient record 508 in order to optimize neurostimulation and provide a log of patient information. A physician may access the patient record 508 to determine correlation between any of the environmental conditions and inflammation in order to reduce patient inflammation.

The third class of sensors 506 relate to patient outcomes, such as those that might be included as part of clinical endpoints in trials of anti-inflammatory therapies. In some embodiments, this may include patient-reported outcomes, indicating how they feel in relation to the chronic inflammation they may be experiencing, or other issues that the inflammation may be causing. In other embodiments, third class of sensors 506 may be configured to monitor patient outcomes directly without requiring the input of the patient. In some embodiments, patient input for the third class of sensors 506 may include information including general quality of life, sleep quality, symptom severity, activity level, mood, documentation of life events identified as important/relevant by the patient, or other such experimental information. In some embodiments, the information from the third class of sensors 506 may be input into the patient record 508 and may be used to determine the effectiveness of stimulation delivered by the neurostimulator 12 in the eyes of the patient.

In some embodiments, the third class of sensors 506 may be used to determine information regarding sleep quality issues of the patient, which may include movement or interruption of sleep, insufficient sleep hours, inconsistent sleep schedules, inadequate amount of time spent in particular sleep stages, or excessive sleep. As previously discussed, sleep quality issues have been known to increase inflammation by increasing plasma levels of pro-inflammatory cytokines, such as IL-6. Additionally, sleep quality issues are often common in IMID's such as psoriasis, RA, and inflammatory bowel disease (IBD). In particular, it is known in the art that there is an increased risk of sleep apnea in patients with psoriasis. Thus, sleep quality issues may trigger inflammation, and in a reverse aspect inflammatory diseases may cause further sleep quality issues. The association between sleep quality issues is often severity dependent, such that the severity of the sleep quality issues relates directly to the severity of the IMID's. In some embodiments, the third class of sensors 506 may be configured to monitor the sleep quality of the patient. The third class of sensors 506 may comprise movement sensors, such as accelerometers and inclinometers, to estimate the subject's sleep/wake state, as well as their movement throughout the sleep state, in order to determine the sleep quality of the patient.

The combination of data in the patient record 508 received by the first, second, and third classes of sensors 502-506 may be used to provide a central source of patient information, which may be accessible both by a physician and a patient. The patient record 508 can be reviewed by the physician in order to make alterations to the programming of the neurostimulator 12 in order to deliver the most appropriate therapy. In some embodiments, the patient record 508 may automatically issue alarms if certain variables migrate outside of a predetermined range, potentially enabling emergent situations to be averted. In some embodiments, the first class of sensors 502 and second class of sensors 504 may be used in conjunction to notify a patient as to which of their habits may be cause increased inflammation. For example, if the first class of sensors 502 detects increased inflammation based on the monitored biomarkers of inflammation, such as heart rate, it may be correlated with data received from the second class of sensors 504 to determine what might be causing the surge in inflammation. In some cases, a change in climate or diet may affect inflammation. The cause of the inflammation can be identified by cross-correlating the information from the first class of sensors and the second class of sensors 504, and may update the patient record 508 to alert the physician and the patient as to what activities might be harming the patient, and may provide a recommendation to the patient in order to reduce their inflammation.

In some embodiments, the third class of sensors 506 may be used in conjunction with the first class of sensors 502 and/or the second class of sensors 504 in order to determine how the patients' perceptions relate to actual conditions detected by the first or second class of sensors 502, 504. For example, the patient may track their symptom severity, particularly in relation to inflammation, using the third class of sensors 506. This can be cross-correlated with data from the first class of sensors 502, which includes biomarkers of inflammation, to determine a degree of inflammation during the same time period. If there is a discrepancy between the detected level of inflammation by the first class of sensors 502 and patients perceived inflammation severity level input by the third class of sensors 506, the second class of sensors 504 may be used to determine what environmental conditions might be making the inflammation symptoms seem worse for the patient. For example, perhaps certain foods may trigger the patient and make the inflammation seem far more severe to the patient than is actually being monitored by the first class of sensors 502. This may provide an alert, via the patient record 508, to notify the patient to modify their diet in order to reduce their symptoms.

In some embodiments, the third class of sensors 506 may be used in conjunction with the first class of sensors 502 and/or the second class of sensors 504 in order to determine the correlation of sleep quality issues and inflammation. For example, the first class of sensors 502 may monitor the ventilation rate of the patient. It is known that a drop in ventilation may correspond to an apnea or hypopnea. The third class of sensors 506 may monitor the movement of the patient at the same time as the drop in ventilation. The drop in ventilation in combination with feedback from the third class of sensors 506 may indicate that the patient is experiencing problems with sleep quality, such as a sleep apnea. In response to determining that the patient is experiencing sleep apnea in addition to inflammation, stimulation may be delivered in order to simultaneously relieve the patient of inflammation and to improve the patient's sleep quality. For example, it is known that the pharyngeal branch of the vagus nerve can influence airway patency, and that during periods of VNS patients may experience some airway constriction and obstructive sleep apnea. Alternatively, the neurostimulator 12 may proceed with VNS and simultaneously stimulate a second nerve in order to relieve the patient of the airway constrictions. Thus, sleep tracking by the third class of sensors 506 provides an opportunity to coordinate therapy in order to treat inflammation, as well as relieve sleep quality issues which may be associated with inflammation.

In some embodiments of the present invention, the neurostimulator 12 may be configured to stimulate multiple nerves of the patient 100 in order to optimize the reduction of inflammation. Both efferent and afferent pathways contribute to suppressing inflammation, therefore it may be beneficial to have a system which modulates portions of both the efferent and afferent pathways by stimulation of multiple nerve pathways. In some embodiments, the neurostimulator 12 may be configured to selectively stimulate two or more of the vagus nerve, the carotid sinus nerve, the aortic depressor nerve, the greater splanchnic nerve, and the splenic nerve. For example, in one non-limiting embodiment the neurostimulator 12 may be configured to stimulate the greater splanchnic nerve, as the greater splanchnic nerve may actually be the pathway by which the inflammatory reflex operates, as well as the carotid sinus nerve, which is known to reduce systemic inflammation. The nerves may be stimulated either directly on the surface or via field stimulation from a nearby structure (e.g. the sympathetic ganglia may be stimulation from a location near the spines). In some embodiments, different forms of energy may be used for stimulation, such as electricity, light, vibration, and sound. Additionally, nerves with transduction capabilities, such as the carotid sinus nerve, may be stimulated indirectly by applying energy which is transduced into nerve excitation, or in this case stretch. In some embodiments, stimulation of multiple nerves may occur by neurostimulator 12. In other embodiments, various systems may be used, which include multiple leads or multiple electrode assemblies off of a single lead. In some embodiments, the stimulation parameters, such as the amplitude, frequency, pulse width, duty cycle, polarity, and number of active sites of stimulation, for both electrode assemblies may be the same. In other embodiments, the stimulation parameters of the electrode assemblies may differ, such that the stimulation of each nerve is identical to that nerve. In some embodiments, such as the case of simultaneous stimulation of the cervical vagus verve and the carotid sinus nerve, a combined lead may have a substantially "Y" shape, such that one of the arms extends to the cervical vagus nerve and the other arm extends to the carotid sinus nerve. In some embodiments, the arms may be of different lengths. Each arm of the lead may include multiple electrodes, in various configurations, to allow for electronic repositioning of the stimulation vector in order to selectively activate target fibers within the nerve. In other embodiments, a "Y" shaped lead may be used for simultaneous stimulation of multiple nerves within the abdomen, such as the abdominal vagus nerve and the greater splanchnic nerve. In still other embodiments, the lead may have different shapes and different configuration of electrodes for stimulation of multiple nerves.

In some embodiments, the neurostimulator 12 may be configured to deliver stimulation both for the treatment of inflammation, which may be a result of IMID's, as well as to improve sleep quality of the patient if it determined by the sensors that the patient experiences sleep quality issues. In correlation to modifying stimulation based on the circadian rhythm of the patient, sensor 31 or the first class of sensors 502 may be used to determine whether the patient is in a sleep state or an awake state. When the patient is in a sleep state, the third class of sensors 506 can be used to monitor the quality of the patient's sleep, and determine any sleep quality issues such as poor quality sleep (due to excessive movement/interruption), insufficient sleep hours, inconsistent sleep schedules, inadequate amount of time spent in the various sleep stages, excessive amounts of sleep, or sleep disorders such as apnea and hypopnea. If it is determined that there are sleep quality issues, the neurostimulator 12 may modify the delivery of stimulation or may begin delivering stimulation to a secondary nerve in order to target the improvement of sleep quality. In some embodiments, the stimulation for the treatment of inflammation may comprise a different set of parameters than the stimulation for the treatment of sleep quality issues. The neurostimulator 12 may comprise components in order to stimulate a first nerve according to a first set of parameters and a second nerve according to a second set of parameters, wherein the first set of parameters and the second set of parameters are different. In other embodiments, multiple nerves may be stimulated according to the same parameters.

Figure 6:
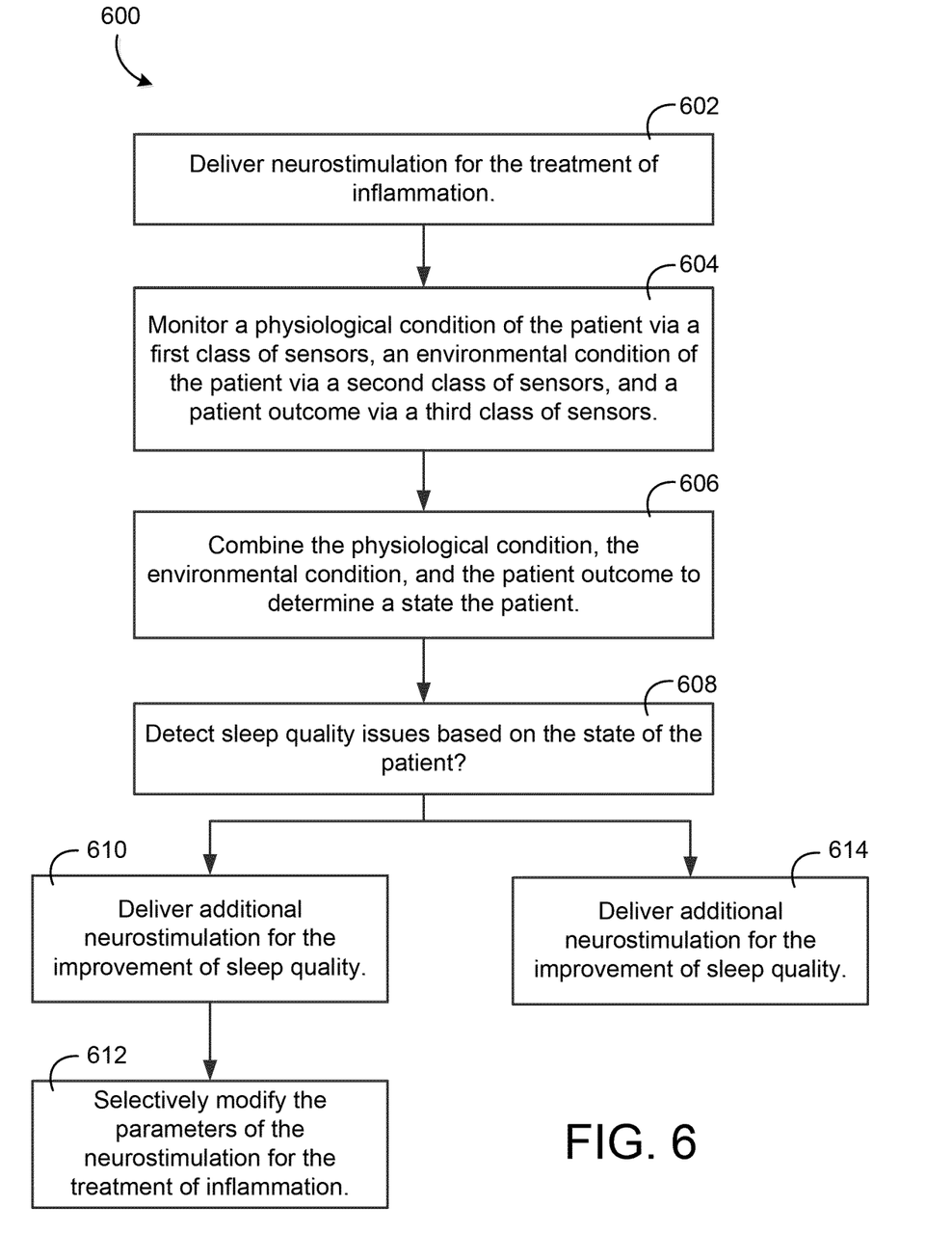
FIG. 6 is a flowchart of a process for modifying the delivery of neurostimulation, according to an exemplary embodiment.

Referring now to FIG. 6, an exemplary method 600 for the delivery of neurostimulation in order to target inflammation and sleep quality issues is shown, according to an exemplary embodiment. The method begins by delivering neurostimulation for the treatment of inflammation (602), wherein the inflammation may be associated with an IMID. In some embodiments, the neurostimulation may be VNS, although stimulation of any of the nerves as discussed above is possible. During delivering of the neurostimulation, each of the three classes of sensors 502-506 discussed above monitors the physiological condition of the patient, the environmental condition of the patient, and the patient outcomes, respectively (604). The feedback from one or more of the classes of sensors 502-506 is then combined to determine a state of the patient (606). In some embodiments, the state of the patient refers to an awake state or a sleep state. In other embodiments, the state of the patient refers to a physical condition, such as if they are experiencing a sleep quality issue such as apnea/hypopnea. The method then determines whether or not the patient is experience sleep quality issues (608). If the patient is experiencing sleep quality issues, the method begins delivering additional neurostimulation for the improvement of sleep quality (610). The additional neurostimulation may include stimulation of a secondary nerve in addition to the nerve already being stimulation for the treatment of inflammation. In some embodiments, the secondary nerve may be the hypoglossal nerve, and additional stimulation may be provided to the hypoglossal nerve in order to reduce airway constriction and obstruction, which may be contributing to the sleep quality issues. In other embodiments, the secondary nerve may be a glossopharyngeal nerve, a pharyngeal nerve, or any of the nerves discussed previously. Additionally, the method comprises selectively modifying the parameters of the neurostimulation for the treatment of inflammation in response to detecting sleep quality issues (612). The neurostimulation of the first nerve may be modified such that the stimulation is at a higher frequency than the stimulation of the second nerve, as higher-frequency stimulation may preserve airway patency when constriction might otherwise occur. In some embodiments, the high frequency stimulation of the first nerve may be triggered upon detection of a breathing disturbance of the patient, which may be determined by the first class of sensors 604. In other embodiments, other parameters of the neurostimulation of the first nerve may be modified in order to optimally treat both the inflammation and improve sleep quality. If no sleep quality issues have been detected, the method may continue delivering neurostimulation for the treatment of inflammation (614).

According to some embodiments, stimulation of multiple nerves may have a variety of benefits for anti-inflammatory therapy over stimulation of a single nerve. In one embodiment, stimulation of multiple nerve sites will increase the amount of signaling in order to generate a greater anti-inflammatory therapeutic effect. Increased signaling of the target structures can be accomplished in a variety of ways. In one embodiment, stimulation of target structures may be increased by directly stimulating nerves which innervate the target structures. For example, simulation of the efferent trunk in both the vagus and sacral nerves directly innervates the gut. In order to target inflammation of the gut, stimulation of both the vagus and sacral nerve simultaneously may be beneficial. In other embodiments, it may be possible to increase stimulation of target centers by stimulating multiple nerves which have the same target center. For example, stimulation of afferent traffic to the central nervous system can be accomplished by stimulation of both the vagus nerve and the carotid sinus nerve. Stimulation of both these nerves will cause an increase in afferent traffic to the central nervous system to optimize potential benefits. In still other embodiments, a combination of both methods of increase stimulation may be used.

According to another embodiment, stimulation of multiple nerves may further act to diversify the signaling pathway to reduce the possibility of acclimatization. There is a possibility that repetitively stimulating a nerve may cause stimulation of that nerve to become less effective over time. This may in part be due to responsiveness of the nerve itself or may be due to processing that occurs later in the circuit via the various feedback mechanisms. Stimulation of multiple nerves would allow for the alternation between various pathways and may help to prevent the possibility of acclimatization. For example, stimulation could occur on a predetermined schedule or may be modified regularly by a physician in order to avoid this phenomenon. In some embodiments, a physician may rotate between stimulation of the vagus nerve and the sacral nerves in order to innervate the gut.

According to another embodiment, stimulation of multiple nerves may further act to provide redundant signaling in order to address potential shortcomings. Neural interfaces may evolve over time due to surgical healing and a variety of other factors. As the neural interfaces evolve, they become less effective, such that stimulation of a nerve site is not as effective as it once was. A physician may not always immediately notice the degradation of the neural interface and the cause behind the stimulation not being as effective may not be immediately identified. Additionally, an implanted stimulation system may have deficiencies over time due to normal wear, such as lead damage. The use of multiple implanted stimulation systems provides a failsafe method such that when stimulation of one nerve starts to fail, either due to degradation of the neural interface or damage to the system, that another nerve can be immediately stimulated to prevent against possible repercussions.

According to another embodiment, stimulation of multiple nerves may help to balance signaling to the central nervous system and targets. IMIDs typically involve localized inflammation, such as gut inflammation in Inflammatory Bowel Disease, joint inflammation in RA, and skin inflammation in Psoriasis. In addition to the localized inflammation, IMIDs may also cause a background systemic inflammation, such as the increased levels of TNF and IL-6 as described above. Stimulation of both afferent traffic and efferent traffic may help to simultaneously treat both the localized inflammation as well as the system inflammation. For example, stimulation of efferent traffic to an inflamed target structure, such as the efferent sympathetic intestinal plexus traffic, can address the localized inflammation of the target structure. Stimulation of the central nervous system via afferent traffic, such as via the cervical vagus nerve, can simultaneously promote systemic anti-inflammatory conditions. In other embodiments, it may be desirable to maintain an anti-inflammatory state in a localized position while at the same time allowing for a degree of systemic inflammation. For example, in the gut of a patient with inflammatory bowel disease, it is desirable to maintain an anti-inflammatory state within the gut. At the same time, it is beneficial to allow for a degree of systemic inflammation in order to better allow the body to defend against systemic infectious pathogens. It is beneficial to treat one type of inflammation while allowing other inflammation to remain present by stimulating multiple nerve sites. Thus provides one benefit over traditional drug therapies, as traditional drug therapies suppress both the localized response and the systemic immune response, often leaving patients prone to opportunistic infections.

According to yet another embodiment, stimulation of multiple nerves may allow for localized signaling to targets of interest in order to minimize side effects of the stimulation. In nerves such as the cervical vagus or greater splanchnic nerves, the branches of the nerves extend to a large number of different organs. Thus stimulation of the nerve can induce changes in a wide range of physiologic processes based on all of the different organ functions. This provides a disadvantage, in that certain organs may be stimulated which are not the original target. In traditional cervical vagus nerve stimulation, side effects often result in symptoms such as voice alteration and discomfort in the neck. In stimulation of the greater splanchnic nerve, side effects may involve alterations in blood pressure due to changes in sympathetic nerve traffic in arterial and venous smooth muscle, which are stimulated via similar target structures. Thus, there are advantages to localizing stimulation to affect traffic on a limited number of targets in order to prevent from adverse side effects, while still maintaining stimulation of multiple nerve sites in the localized mechanism. Stimulation may be localized by a variety of different mechanisms, depending on the location of the stimulation. According to one embodiment, stimulation of the suprahepatic branch of the vagus nerve will affect both afferent and efferent signaling associated with the gut and the liver in order to treat inflammatory bowel disease. According to another embodiment, stimulation of the splenic nerve will influence neurotransmitter effects on macrophages resident within the spleen, which addresses both systemic and localized inflammation. According to another embodiment, the sacral nerve may be stimulated to affect afferent and efferent signaling associated with the distal colon. In still another embodiment, the sympathetic nerves innervating a specific inflamed joint in RA may be stimulated to affect inflammation therein. The various described benefits of localized stimulation, as well as the example embodiments described herein, may be used in conjunction with multi-site nerve stimulation to more effectively target the specific symptoms of each associated disease.

In some embodiments of the present invention, the neurostimulator 12 may also be configured to stimulate one or more nerves of the patient 100 in order to optimize the reduction of inflammation in relation to cardiovascular disease. VNS has been proposed as therapy for heart failure, one of the components of cardiovascular disease responsible for the higher death rate in RA patients. As IMIDs and cardiovascular diseases are linked, it is optimal to treat both via stimulation. In some embodiments, any of the three classes of sensors 502-506 may be used to gather information related to cardiovascular disease, such as heart rate, and to provide stimulation accordingly. In some embodiments, neurostimulator 12 may be used to stimulate a patient for treatment of both chronic inflammation and cardiovascular disease. In still other embodiments, multiple nerves may be stimulated, as described above, to efficiently treat both inflammation and cardiovascular disease. According to one non-limiting example, the splenic nerve may be modulated to treat chronic inflammation due to IMIDs while simultaneously the vagus nerve may be stimulated to treat symptoms of cardiovascular disease. According to another non-limiting example, the carotid sinus nerve may be stimulated in combination with the vagus nerve, as stimulation of the carotid sinus nerve has been shown to reduce blood pressure and to improve symptoms of heart failure. Various stimulation parameters, such as the amplitude, frequency, pulse width, duty cycle, polarity, and number of active sites of stimulation, may be modified based on the measured characteristics of both the IMID and the cardiovascular.

While various aspects and embodiments have been disclosed herein, other aspects and embodiments will be apparent to those skilled in the art. The various aspects and embodiments disclosed herein are for purposes of illustration and are not intended to be limiting.

What is claimed is:

1. A method of modulating the nervous system to reduce inflammation, comprising:
    delivering a vagus nerve stimulation (VNS) therapy to a vagus nerve of a patient for the treatment of inflammation according to a first set of parameters; and
    delivering a secondary nerve stimulation (SNS) therapy to a secondary nerve of the patient for the treatment of a sleep disorder according to a second set of parameters different from the first set of parameters, wherein the secondary nerve is different than the vagus nerve.

2. The method of claim 1, wherein the secondary nerve comprises one or more of the hypoglossal nerve, the carotid sinus nerve, the aortic depressor nerve, the greater splanchnic nerve, the splenic nerve, the trigeminal nerve, and the paravertebral ganglia of sympathetic nerves.

3. The method of claim 1, further comprising:
    monitoring, via a first sensor, a physiological condition of the patient; and
    modifying at least one of the first set of parameters of the VNS therapy or the second set of parameters of the SNS therapy based on the physiological condition of the patient.

4. The method of claim 3, further comprising:
    estimating when the patient is in an awake state based on the physiological condition; and
    temporarily suspending delivery of the SNS therapy when the patient is in the awake state.

5. The method of claim 3, further comprising:
    monitoring, via a second sensor, an environmental condition of the patient; and
    modifying at least one of the first set of parameters of the VNS therapy and the second set of parameters of the SNS therapy based on a combination of the physiological condition and the environmental condition.

6. The method of claim 5, wherein the environmental condition of the patient corresponds to one or more of an amount of air pollution, a climate condition, and an exposure to sunlight.

7. The method of claim 3, further comprising:
    monitoring, via a third sensor, a patient outcome of the patient; and
    modifying at least one of the first set of parameters of the VNS therapy and the second set of parameters of the SNS therapy based on a combination of the physiological condition and the patient outcome.

8. The method of claim 7, wherein the patient outcome comprises an indication of a sleep quality, and wherein the second set of parameters of the SNS therapy are modified in order to improve the sleep quality.

9. The method of claim 1, wherein the VNS therapy is delivered at a higher frequency than the SNS therapy.

10. A system for modulating the nervous system to reduce inflammation, comprising:
    a pulse generator, wherein the pulse generator generates pulsed electrical signals;
    a lead;
    one or more electrodes communicatively coupled to the pulse generator via the lead, wherein the pulse generator is configured to apply the pulsed electrical signal to one or more nerves via the one or more electrodes; and
    a processor configured to:
        deliver a vagus nerve stimulation (VNS) therapy to a vagus nerve of a patient for the treatment of inflammation via the one or more electrodes according to a first set of parameters; and
        deliver a secondary nerve stimulation (SNS) therapy to a secondary nerve of the patient for the treatment of a sleep disorder via the one or more electrodes according to a second set of parameters different from the first set of parameters, wherein the secondary nerve is different than the vagus nerve.

11. The system of claim 10, wherein the secondary nerve comprises one or more of the hypoglossal nerve, the carotid sinus nerve, the aortic depressor nerve, the greater splanchnic nerve, the splenic nerve, the trigeminal nerve, and the paravertebral ganglia of sympathetic nerves.

12. The system of claim 10, further comprising a first sensor configured to monitor a physiological condition of the patient, and wherein the processor is further configured to modify at least one of the first set of parameters of the VNS therapy or the second set of parameters of the SNS therapy based on the physiological condition of the patient.

13. The system of claim 12, wherein the processor is further configured to estimate when the patient is in an awake state based on the physiological condition and temporarily suspend delivery of the SNS therapy when the patient is determined to be in the awake state.

14. The system of claim 12, wherein the first sensor comprises one or more of a heart rate sensor, an accelerometer, a minute ventilation sensor, and a core temperature sensor.

15. The system of claim 12, further comprising a second sensor configured to monitor an environmental condition of the patient, and wherein the processor is further configured to modify at least one of the first set of parameter of the VNS therapy and the second set of parameters of the SNS therapy based on a combination of the physiological condition and the environmental condition.

16. The system of claim 12, further comprising a third sensor configured to monitor a patient outcome of the patient, and wherein the processor is configured to modify at least one of the first set of parameters of the VNS therapy and the second set of parameters of the SNS therapy based on a combination of the physiological condition and the patient outcome.

17. The system of claim 16, wherein the patient outcome comprises an indication of a sleep quality and wherein the second set of parameters of the SNS therapy are modified in order to improve the sleep quality.

18. The system of claim 11, wherein the VNS therapy is delivered at a higher frequency than the SNS therapy.

19. A non-transitory computer-readable medium having instructions stored thereon that are executable by a processor of an implantable neurostimulation system to cause the processor to perform operations comprising:
- delivering a vagus nerve stimulation (VNS) therapy to a vagus nerve of a patient for the treatment of inflammation according to a first set of parameters; and
- delivering a secondary nerve stimulation (SNS) therapy to a secondary nerve of the patient for the treatment of a sleep disorder according to a second set of parameters different from the first set of parameters, wherein the secondary nerve is different than the vagus nerve.

20. The non-transitory computer-readable medium of claim 19, wherein the processor is further configured to perform operations comprising:
- monitoring, via one or more sensors, a physiological condition of the patient and a patient outcome; and
- modify at least one of the first set of parameters of the VNS therapy and the second set of parameters of the SNS therapy based on a combination of the physiological condition and the patient outcome.

* * * * *